(12) United States Patent
Finkel

(10) Patent No.: US 9,980,642 B2
(45) Date of Patent: May 29, 2018

(54) APPARATUS AND METHOD FOR DETERMINING PHYSIOLOGIC PERTURBATIONS OF A PATIENT

(71) Applicant: CHILDREN'S NATIONAL MEDICAL CENTER, Washington, DC (US)

(72) Inventor: Julia C Finkel, Washington, DC (US)

(73) Assignee: CHILDREN'S NATIONAL MEDICAL CENTER, Washington, DC (US)

(*) Notice: Subject to any disclaimer, the term of this patent is extended or adjusted under 35 U.S.C. 154(b) by 0 days. days.

(21) Appl. No.: 14/491,745

(22) Filed: Sep. 19, 2014

(65) Prior Publication Data

US 2015/0116665 A1    Apr. 30, 2015

Related U.S. Application Data

(60) Provisional application No. 61/879,707, filed on Sep. 19, 2013.

(51) Int. Cl.
*A61B 3/113* (2006.01)
*A61B 3/11* (2006.01)
(Continued)

(52) U.S. Cl.
CPC .............. *A61B 3/112* (2013.01); *A61B 3/0025* (2013.01); *A61B 3/11* (2013.01); *A61B 3/145* (2013.01); *A61B 5/031* (2013.01)

(58) Field of Classification Search
CPC ........... A61B 3/00–3/185; A61B 5/031; A61B 3/0025; G06F 3/013; A61F 2009/00846
(Continued)

(56) References Cited

U.S. PATENT DOCUMENTS 5,187,506 A    2/1993  Carter
7,487,524 B2 *  2/2009  Miyamori ......... G06F 17/30843
                                              382/100
(Continued)

OTHER PUBLICATIONS

International Search Report and Written Opinion dated Dec. 29, 2014 in PCT/US2014/056579.
(Continued)

*Primary Examiner* — Bumsuk Won
*Assistant Examiner* — Henry Duong
(74) *Attorney, Agent, or Firm* — Oblon, McClelland, Maier & Neustadt, L.L.P.

(57) ABSTRACT

The present disclosure is related to a method and apparatus for determining a physiologic perturbation of a patient including acquiring a video sequence, including a plurality of video frames, of an eye of a patient, selecting at least one parameter of a plurality of parameters including a baseline pupil size, a maximum change in size of a pupil, an average velocity of constriction of the pupil, a maximum velocity of constriction of the pupil, latency of constriction of the pupil, and a velocity of re-dilation of the pupil, determining, using processing circuitry and based on the plurality of video frames, the selected at least one parameter of the plurality of parameters, and determining the physiologic perturbation of the patient based on the determined at least one parameter, where the least one parameter of the plurality of parameters is selected based on which physiologic perturbation of the patient is to be determined.

23 Claims, 6 Drawing Sheets

(51) Int. Cl.
    *A61B 3/00*     (2006.01)
    *A61B 3/14*     (2006.01)
    *A61B 5/03*     (2006.01)

(58) Field of Classification Search
    USPC ............... 351/200–206, 208–211, 222, 246
    See application file for complete search history.

(56) References Cited

U.S. PATENT DOCUMENTS

| | | | |
|---|---|---|---|
| 8,235,526 B2 * | 8/2012 | Stark | A61B 3/112 |
| | | | 351/205 |
| 8,393,734 B2 | 3/2013 | Privitera et al. | |
| 8,534,840 B2 | 9/2013 | Siminou | |
| 2004/0246441 A1 | 12/2004 | Stark et al. | |
| 2009/0174865 A1 | 7/2009 | Privitera et al. | |
| 2010/0312139 A1 * | 12/2010 | Dash | G01N 33/6893 |
| | | | 600/561 |
| 2011/0228224 A1 | 9/2011 | Siminou | |
| 2014/0135590 A1 * | 5/2014 | Pedro | A61B 5/0205 |
| | | | 600/301 |

OTHER PUBLICATIONS

Extended European Search Report dated Jun. 7, 2017 in Patent Application No. 14784565.5.

Combined Office Action and Search Report dated Apr. 17, 2017 in Chinese Patent Application No. 201480057795.8 (with English translation).

Office Action dated Jan. 8, 2018 in Chinese Patent Application No. 201480057795.8 (with English translation).

* cited by examiner

APPARATUS AND METHOD FOR DETERMINING PHYSIOLOGIC PERTURBATIONS OF A PATIENT

CROSS-REFERENCE TO RELATED APPLICATIONS

This application is based upon and claims the benefit of priority under 35 U.S.C. § 119(e) from U.S. Ser. No. 61/879,707, filed Sep. 19, 2013, the entire contents of which are incorporated herein by reference.

FIELD OF THE INVENTION

This disclosure is related to an image capture device configured to capture a video image of the eye (including the iris and pupil), method of detecting a pupil and an iris of an eye on the video image, method of determining both static and dynamic measurements of the pupil and the iris, and a method of determining drug usage or a medical condition of a patient based on the static and dynamic measurements of the pupil and the iris.

BACKGROUND

Control of the pupil is a complex physiology that involves multiple neuronal pathways, and pupillary behavior is the reflection of the integrity and functionality of neurological circuits. Measurement of pupil size and dynamic response to light can reflect alterations or abnormalities in the metabolism or the structure of the central nervous system. Such determinations are important in both experimental and clinical settings.

Pupil assessment is a routine practice in medical care, used in a variety of settings, ranging from first responders to intensive care units. Currently, pupil assessment is most commonly performed using a penlight. While this is an easy assessment method, the results remain subjective and variable with operator expertise. The information generated by the penlight is limited to gross pupil features, such as presence or absence of light reflex and estimation of pupil size and symmetry. Subtle changes cannot be assessed, and these are important tools to track clinical conditions such as brain trauma and viability following cardiac or pulmonary arrest. Accurate pupil measurement can also be used to monitor drug use and abuse, tolerance and opioid hyperalgesia.

The "background" description provided herein is for the purpose of generally presenting the context of the disclosure. Work of the presently named inventor, to the extent it is described in this background section, as well as aspects of the description which may not otherwise qualify as prior art at the time of filing, are neither expressly or impliedly admitted as prior art against the present invention.

SUMMARY

An exemplary embodiment of the present disclosure describes an apparatus (a smart phone based pupillometer device) that combines an infra-red camera (e.g. PupilCam) contained in a chamber attachment to a smart phone, with applications that will enable objective measurement of pupil size and dynamic behavior in the clinical setting. The infra-red camera attachment will be adaptable to fit the patients face to facilitate accurate pupil assessment by a ubiquitous device. The device will be a screening tool and specific applications will contain algorithms/methods developed to address different clinical situations.

A device according to an exemplary embodiment is both an application for smart phones and hardware (chamber to adapt the smart phone to the patient's face). Pupillometers have been used in ophthalmology and many other medical fields to evaluate pupil's size and reactivity. The devices currently available have not gained broader clinical use because they are expensive, stand-alone devices that provide raw data without interpretation, so they require a trained professional to evaluate the readings, synthesize the information and guide appropriate interventions.

A method and apparatus according to an exemplary embodiment will enable clinicians and health care professionals to assess, precisely and objectively, pupil dynamic measurements and compare these parameters over time using different algorithms specific to different clinical situations. The application format on the smart phone will also enable objective generation of comparative information to facilitate the understanding of the generated data. The device also will permit certain, limited assessments by laypersons to determine the need for further medical intervention.

The apparatus and method according to an exemplary embodiment provide an objective measurement of pupil responsiveness in clinical situations. The apparatus and method according to an exemplary embodiment will replace both current assessment tools: the penlight which is imprecise and subjective, and existing clinical pupillometer devices, which are prohibitively expensive and whose objective measurements require an expert trained to synthesize and interpret the results.

The apparatus and method according to an exemplary embodiment provide ready access to data that are important tools in different clinical situations, integrating the chamber (described as mount interface below), adjustable to the patient's face, with the smartphone as a processor of the collected information. Specific algorithms will interpret the data, adjusting to different clinical situations, and allowing wide use and access by different medical professionals and laypersons.

Among multiple applications, the assessment of pupil dynamics applied to opioid use presents one of the greatest opportunities for broader use of pupillometry. Opioids cause pupillary constriction by excitation of the parasympathetic innervations of the pupil. Thus, opioid-related miosis is thought to be the most sensitive indicator of mu-receptor-mediated efficacy. Miosis has been shown to be strictly dose dependent with various opioids, which explains the common occurrence of 'pinpoint' pupils in opioid exposure. In addition, a relationship has been shown between opioid concentrations in plasma and pupil diameter. With these known correlations, the apparatus and method according to an exemplary embodiment will be an important tool to evaluate patients at the beginning of the opioid therapy and track the evolution of the treatment assessing compliance, tolerance, abuse and hyperalgesia status.

Another important application related to opioid use is the pupillary assessment of noxious stimulation and analgesia during surgery under general anesthesia. Referring to chronic use of opioids, the pupillary assessment can also be used to monitor and diagnose, among other clinical features, withdrawal abstinence syndrome in patients or babies from mothers that use opioids.

BRIEF DESCRIPTION OF THE DRAWINGS

A more complete appreciation of the disclosed embodiments and many of the attendant advantages thereof will be readily obtained as the same becomes better understood by reference to the following detailed description when considered in connection with the accompanying drawings, wherein.

DETAILED DESCRIPTION

Figure 1:
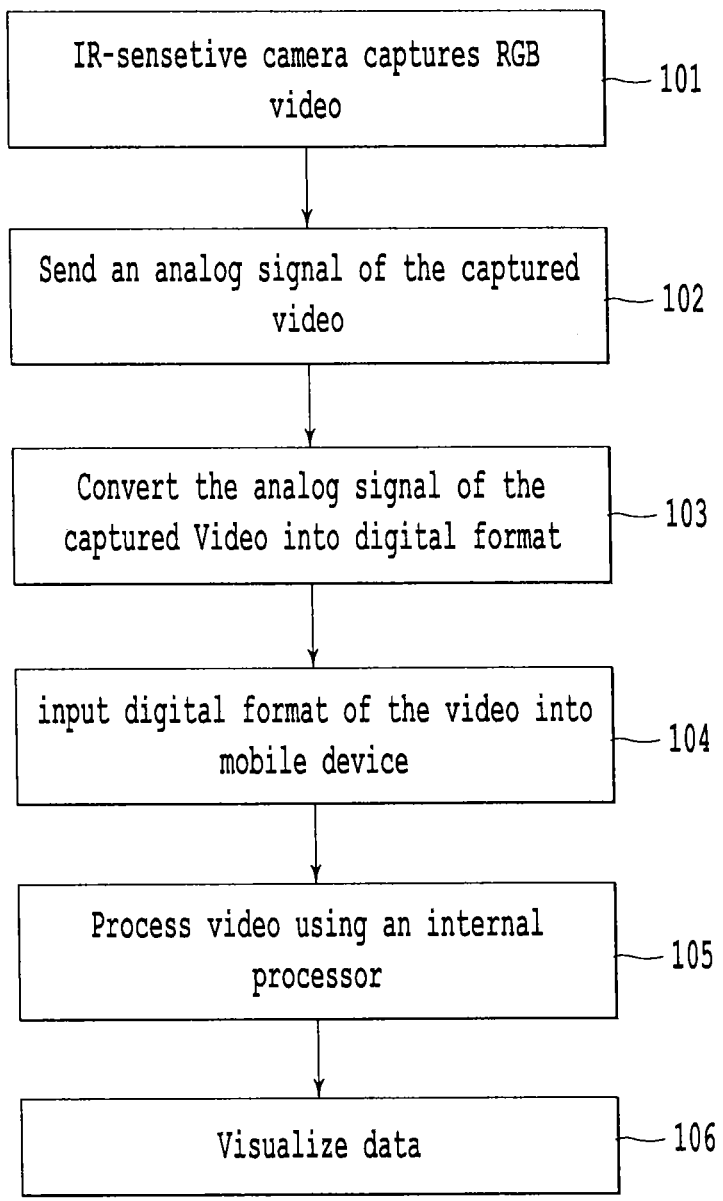
FIG. 1 illustrates an overview of a method of detecting the iris and the pupil of an eye according to an exemplary embodiment.

The present embodiments are related to a method of determining a physiologic perturbation of a patient. The method includes the steps of acquiring a video sequence, including a plurality of video frames, of an eye of a patient, selecting at least one parameter of a plurality of parameters including a baseline pupil size, a maximum change in size of a pupil, an average velocity of constriction of the pupil, a maximum velocity of constriction of the pupil, latency of constriction of the pupil, and a velocity of re-dilation of the pupil, determining, using processing circuitry and based on the plurality of video frames, the selected at least one parameter of the plurality of parameters, and determining the physiologic perturbation of the patient based on the determined at least one parameter, where the least one parameter of the plurality of parameters is selected based on which physiologic perturbation of the patient is to be determined.

The method further comprises localizing, in a first frame among the plurality of frames, a center of the pupil and two points on a boundary of the pupil and the iris, generating, using the processing circuitry, a mask image corresponding to an expected location of the iris based on said localizing, said mask image include a plurality of pixels, and determining the at least one parameters based on the generated mask image.

The method further comprises determining, using the processing circuitry, an intracranial pressure to be less than 20 mmHg when the maximum change in the size of the pupil is determined to be greater than 50%, determining, using the processing circuitry, an intracranial pressure to be greater than 20 mmHg when the maximum change in the size of the pupil is determined to be less than or equal to 10%, determining, using the processing circuitry, a midline shift when the maximum change in the size of the pupil is determined to be less than or equal to 10%, determining, using the processing circuitry, an intracranial pressure to be greater than 20 mmHg when the average velocity of constriction of the pupil is less than 0.6 mm/sec.

The method further comprises acquiring a first video sequence of the eye of the patient while the patient is in a supine position, determining, using the processing circuitry and based on the first video sequence, a first version of the selected at least one parameter of the plurality of parameters, acquiring a second video sequence of the eye of the patient while the patient is in an upright position, determining, using the processing circuitry and based on the second video sequence, a second version of the selected at least one parameter of the plurality of parameters, and determining, using the processing circuitry, whether the patient has postural orthostatic tachycardia syndrome (POTS) based on a comparison of the first and the second version of the selected at least one parameter of the plurality of parameters, wherein the second video sequence is acquired a predetermined amount of time after the patient gets to the upright position from the supine position.

The method further comprises determining, using the processing circuitry, that the patient has POTS when the patient's maximum pupil diameter measured in the supine position is 2.5% greater than the patient's maximum pupil diameter measured in the upright position, or determining, using the processing circuitry, that the patient has POTS when the patient's minimum pupil diameter measured in the supine position is 6.7% greater than the patient's minimum pupil diameter measured in the upright position.

The method further comprises determining, using the processing circuitry, that the patient has POTS when the patient's first change in size of the pupil is 8.5% less than the second change in size of the pupil, or determining, using the processing circuitry, that the patient has POTS when the patient's first average velocity of constriction of the pupil is 7.3% less than the second average velocity of constriction of the pupil, wherein a flash embedded in a mobile device is used to stimulate the eye for measuring a degree of dilation and constriction.

The present embodiments are also related to an apparatus for determining a physiologic perturbation of a patient. The apparatus includes circuitry that is programmed or configured to acquire a video sequence, including a plurality of video frames, of an eye of a patient, select at least one parameter of a plurality of parameters including a baseline pupil size, a maximum change in size of a pupil, an average velocity of constriction of the pupil, a maximum velocity of constriction of the pupil, latency of constriction of the pupil, and a velocity of re-dilation of the pupil, determine, using processing circuitry and based on the plurality of video frames, the selected at least one parameter of the plurality of parameters, and determine the physiologic perturbation of the patient based on the determined at least one parameter where the least one parameter of the plurality of parameters is selected based on which physiologic perturbation of the patient is to be determined.

The apparatus includes the circuitry configured to determine an intracranial pressure to be less than 20 mmHg when the maximum change in the size of the pupil is determined to be greater than 50%, determine an intracranial pressure to be greater than 20 mmHg when the maximum change in the size of the pupil is determined to be less than or equal to 10%, determine a midline shift when the maximum change in the size of the pupil is determined to be less than or equal to 10%, and determine an intracranial pressure to be greater than 20 mmHg when the average velocity of constriction of the pupil is less than 0.6 mm/sec.

The apparatus includes the circuitry is configured to acquire a first video sequence of the eye of the patient while the patient is in a supine position, determine, using the processing circuitry and based on the first video sequence, a first version of the selected at least one parameter of the plurality of parameters, acquire a second video sequence of the eye of the patient while the patient is in an upright position, determine, using the processing circuitry and based on the second video sequence, a second version of the selected at least one parameter of the plurality of parameters, and determine, using the processing circuitry, whether the patient has postural orthostatic tachycardia syndrome (POTS) based on a comparison of the first and the second version of the selected at least one parameter of the plurality of parameters, wherein the second video sequence is acquired a predetermined amount of time after the patient gets to the upright position from the supine position.

The apparatus includes circuitry is configured to determine that the patient has POTS when the patient's maximum pupil diameter measured in the supine position is 2.5% greater than the patient's maximum pupil diameter measured in the upright position, or determine that the patient has POTS when the patient's minimum pupil diameter measured in the supine position is 6.7% greater than the patient's minimum pupil diameter measured in the upright position.

The apparatus includes circuitry configured to determine that the patient has POTS when the patient's first change in size of the pupil is 8.5% less than the second change in size of the pupil, or determine that the patient has POTS when the patient's first average velocity of constriction of the pupil is 7.3% less than the second average velocity of constriction of the pupil.

FIG. 1 illustrates an overview of a method of detecting the iris and the pupil of an eye according to an exemplary embodiment. In order to image the constriction and dilation of a pupil with high contrast against the iris, it is necessary to use infra-red (IR) light within the safe level. Unfortunately, mobile cameras in current smartphones block IR light while passing visible light to improve image quality. Thus, the present embodiment is designed to include an easy mount interface to couple a low-cost IR-sensitive CMOS camera module onto existing mobile devices (the design of the mount interface onto existing mobile devices will be described in further detail with regard to FIG. 3). The existing mobile devices can be sensitive to IR light or can be modified to be sensitive to IR light.

In Step 101, a high-quality RGB CMOS camera module, that has six high-power infrared LEDs to light up in the dark can be configured to capture vivid RGB videos at standard definition resolution (the high-quality RGB CMOS camera module can capture vivid RBG videos even in completely dark environments). In Step 102 the camera module sends an RCA analog signal of the captured video to a video capture device. The video capture device is part of the mount interface that receives an analog signal from the camera module. The camera module is easily mountable onto an existing mobile device and should be powered close to a 12V specification. The focal length of 4.3 mm and the aperture of 2.0 of the camera module provide a field of view to 24-100 mm. The flash embedded in a smartphone device can be used for stimulating the eyes for measuring the degree of dilation and constriction of the pupil. Additionally, a modular source can also be used for visual stimulation. The method of the present embodiment can be used to combine pupillary changes to Glasgow Coma Scale (GCS).

In Step 103, the RCA analog signal that is output from the camera module is converted to an MPEG 4 format by the video capture device. It should be noted that the video capture device may convert the RCA analog signal to any audio/video format and the current embodiment is not restricted to the MPEG 4 format. In Step 104, the MPEG 4 format is input to a mobile device, including any of a smartphone device and/or a tablet where an application software is installed, via an embedded universal data I/O interface such as Bluetooth or micro/mini USB. Although the MPEG 4 format is described as being input via an embedded universal data I/O interface such as Bluetooth or micro/mini USB, it should be understood that any wireless/wired communication may be used and the present embodiment is not restricted to any particular wireless/wired communication.

Once data is transferred to the mobile device, the data can be processed using the internal processor (processing circuitry) of the mobile device in Step 105. The processing of the data is described with regard to FIG. 2. Further, in Step 106, a user may visualize data that has been processed by the internal processor of the mobile device. The user may also visualize unprocessed data that is received from the camera module and the video capture device. The RGB image and an IR image captured by the camera module can be overlaid to be viewed by a user. The present embodiment is not limited to localized processing. Sending data to a remote server and returning a result from remote processing may also be utilized.

It should be noted that the camera module is disposable and reusable. Further, the camera module can also be permanently mounted on the mobile device. Although video images are discussed above and below, it should be understood that the camera module can capture both live video streams and still images.

Figure 2:
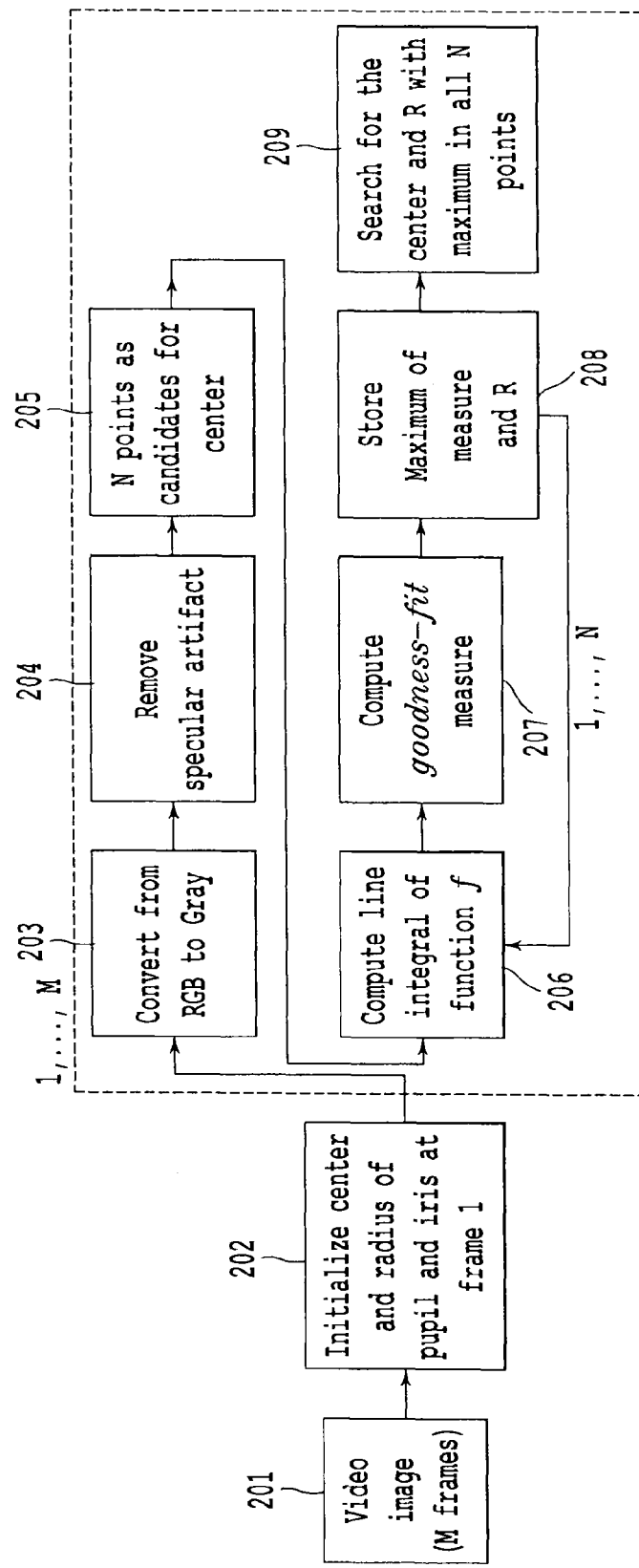
FIG. 2 illustrates a method of detecting the pupil and iris according to an exemplary embodiment.

FIG. 2 illustrates a method of detecting the pupil and iris. All the steps described below with regard to FIG. 2 may be performed by a processor (processing circuitry) of a smartphone device or any external processing device. A video image, including a plurality of frames, is received in Step 201. As noted above with regard to FIG. 1, the video image is captured by the camera module and converted into an MPEG 4 format by the video capture device. Given a video sequence with M frames, each frame of the video sequence is processed to detect the center and the radius of the pupil. In frame 1 (the first frame among the plurality of frames of the video sequence), a user is asked to localize the center and any two points on the boundary of the pupil and the iris as an initialization step (Step 202). A user may view the first frame on a display (such as display of a smartphone device or any display connected to the RGB CMOS camera) and can choose a center point and two points on the boundary of the pupil and the iris. Based on this information, a mask image to cover the expected location of the iris is generated in order to spare computation in an unrelated area (Step 202). The following steps are the same for processing other frames of the video sequence. In Step 203, if necessary, down-sampling of the image video frames is performed for saving computation time. In Step 203 an RGB image frame (video image frame) is converted to a gray scale with double data type ranging from 0 to 1. In Step 204, because bright zones of specular reflection caused by the light source may exist, an additional step that removes the artifact by filling bright pixels with surrounding dark pixels. Bright zones may be removed from the mask image. All the pixels within the mask image are considered candidates for determining the center point of the pupil (Step 205). For example, if the mask image includes N pixels, then all N pixels are considered candidates in determining the center point of the pupil and the iris. A good-of-fit function $f$ as defined below is used to determine the center point and the radius of the pupil and the iris.

$$\sum_{\theta=1}^{n} \left( (n-1) \|g_{\theta,r}\| - \left( \sum_{\phi=\theta+1}^{n} \|g_{\theta,r} - g_{\phi,r}\| \right) - g_{\theta,r}/8 \right)$$

where n stands for the number of discrete values of the polar variable θ that are considered and $g_{\theta,r}$ stands for the directional derivative of image intensity in the radial direction. The first term captures the weighted summed strength of the gradients across the boundary, the second term captures the uniformity of the gradients along the boundary, and the last term captures a slight preference for darker regions on the boundary interior. For each n point in a single video frame, the line integral of function fat distance of [Rmin, Rmax] from the point is computed (Step 206), and after mean filtering two local maxima corresponding to the pupil and the iris each are acquired. A goodness-of-fit measurement is defined as the sum of two peak values (Step 207). The goodness-of-fit measurement and corresponding Rs are stored in memory (Step 208). These procedures are repeated in remaining N−1 points in the mask image. The identified center and radius of the pupil are the ones that maximize goodness-of-fit measurement for all N points (Step 209). For the processing of the next (k+1)th frame, the mask image is updated using the values computed for the k'th frame. In other words, the center and radius of the pupil and the iris calculated for the k'th frame are used to create an updated mask image and steps 202 to 209 are repeated for each additional frame of the video sequence.

Figure 3:
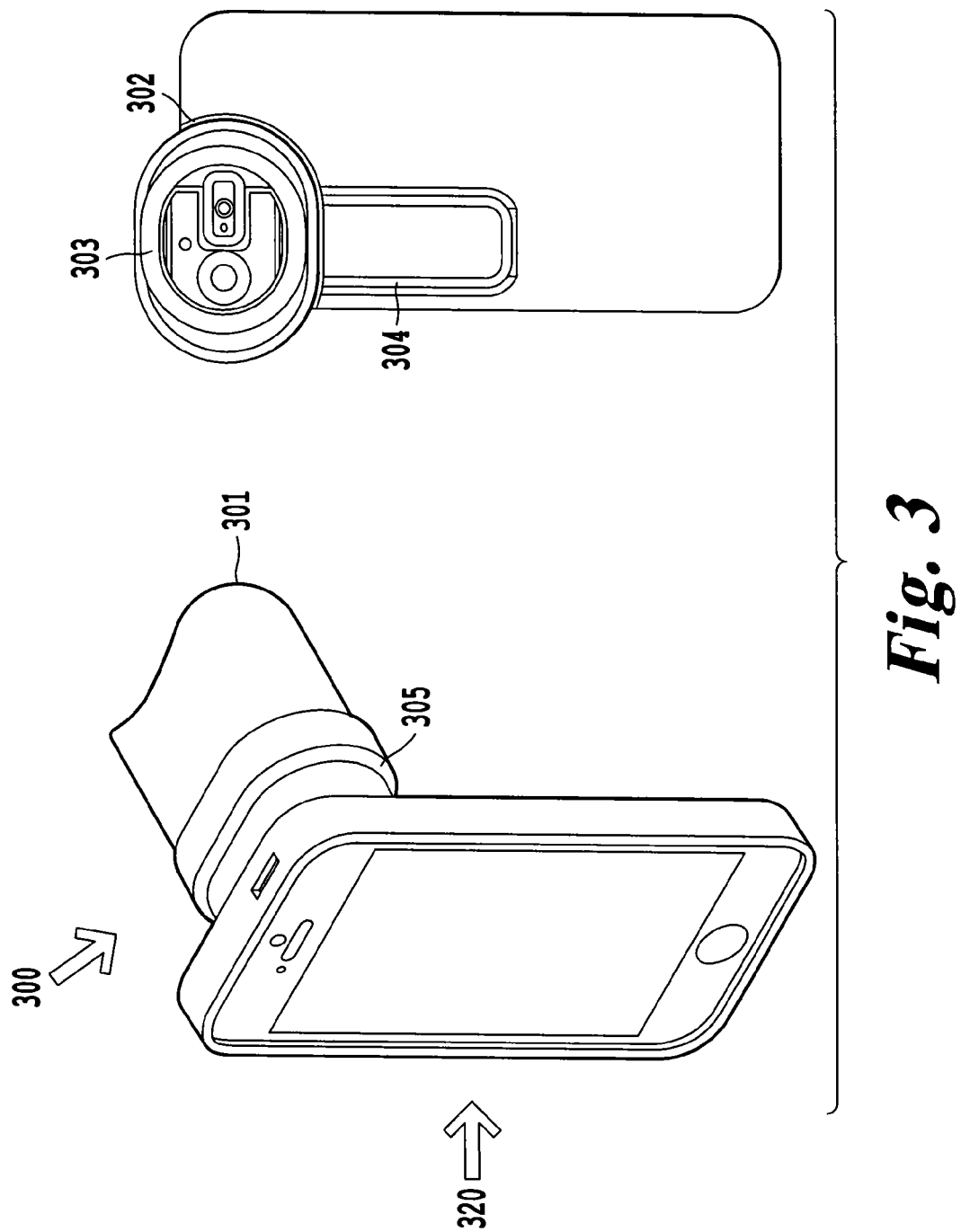
FIG. 3 illustrates a design of the mount interface that is integrated with a smartphone device according to an exemplary embodiment.

FIG. 3 illustrates a design of the mount interface 300 that is integrated with a smartphone device 320. As noted above with regard to FIG. 1, the mount interface 300 includes a low-cost IR sensitive CMOS camera 301 that is coupled to a smartphone device 320. The CMOS camera 301 includes six high-powered infrared LEDs 302 that light up in the dark. Although FIG. 3 illustrates six high-powered infrared LEDs 302, it should be understood that any number of high-powered infrared LEDs may be used.

The CMOS camera 301 further includes a portion 303 into which a human eye is placed so that the human eye can be captured as a video image using the high-powered infrared LEDs 302. The mount interface 300 further includes an attachment 304 that is used to attach the mount interface 300 to the smartphone device 320. The mount interface 300 also includes an intermediate coupling device 305 which is coupled to both the CMOS camera 301 and the attachment 304, as illustrated in FIG. 3. The combination of the mount interface 300 and a smartphone device 320 is useful as a hand-held device to measure pupillary dynamic parameters.

As noted above with regard to FIG. 1, the CMOS camera 301 (using high-powered infrared LEDs 302) can capture vivid RGB videos at standard definition. The captured RGB videos are then sent to a video capture device as an RCA analog signal. The RCA analog signal that is output from the CMOS camera 301 is converted to an MPEG 4 format by the video capture device. It should be noted that the video capture device may convert the RCA analog signal to any audio/video format and the current embodiment is not restricted to the MPEG 4 format. Finally, the MPEG 4 format of the video is input to a mobile device including any of a smartphone device and/or a tablet where the application software is installed, via an embedded universal data I/O interface such as Bluetooth or micro/mini USB. Although the MPEG 4 format is described as being input via an embedded universal data I/O interface such as Bluetooth or micro/mini USB, it should be understood that any wireless/wired communication may be used and the present embodiment is not restricted to any particular wireless/wired communication.

The captured video image is processed by a processor in a smartphone device. Although, a smartphone device is shown in FIG. 3, it should be understood that an external processor (not shown) can also be used to process the capture video image.

The pupillary light reflex (PLR) reflects the integrity of the autonomic nervous system with constriction or miosis occurring in response to a flash of light as a result of increased parasympathetic tone and dilation or midriasis reflecting increased sympathetic tone. The flash of light can be provided by the flash light of a smartphone device. There are at least six pupillometric measures used in the generation of algorithms that can determine a physiologic perturbation such as, for example, usage of drugs or a medical condition. The two static measures include baseline pupil size and the maximally constricted size to generate the constriction amplitude (CON). The baseline pupul size is found before the flash of light and the maximally constricted size is determined after the flash of light. The dynamic responses to a flash of light including the velocity of constriction (average constriction velocity (ACV) and maximum constriction velocity (MCV)), the latency of constriction (LAT), and the velocity of re-dilation are other pupillometric measures. The various parameters of the PLR are impacted in a predictable way by various drugs and medical conditions. The at least six pupillometric measures can be selected based on the application of the measurement. Different applications such as detection of drug use or detection of a medical condition can take into account different pupillometric measures and different amounts of weight or different ways of processing in pupillometric measures.

Heuristic models are used in the development of the algorithms. Quantified data is uploaded and analyzed for patterns that are predictive of a particular scenario. The at least six pupillometric measures can be calculated using a processor (processing circuitry) of a smartphone device or any other device based on the video images acquired by the RGB CMOS camera.

Both the constriction amplitude (CON) and average constriction velocity (ACV) have been determined to be predictive of critical changes in the intracranial pressure (ICP). When CON is measured to be greater than (or equal to) 50%, such a measure indicates that ICP is less than 20 mmHg (millimeters of mercury). Further, when CON is measured to be less than (or equal to) 10%, such a measure indicates that ICP is greater than 20 mmHg or indicates a midline shift of the brain (both of which require immediate attention). Finally, when ACV is measured to be less than 0.6 mm/sec, such a measure can also indicate that ICP is greater than 20 mmHg.

With regard to opioids, all parameters are inversely related to opioid dose with acute administration. With chronic administration, the impact on static measures and ACV reverses, allowing for the identification of tolerance. When the impact on these parameters actually increase from baseline, this is indicative of opioid induced hyperalgesia, a neuro-excitatory condition.

With regard to pain intensity, maximum constriction velocity (MCV) has been shown to correlate with subjective reporting. MCV increases by 0.11 mm/s for every point increase in a 10 point visual analog scale.

The present method can also be used to detect and monitor dysautonomias, which includes a variety of conditions including diabetic neuropathy and postural orthostatic tachycardia syndrome (POTS).

For example, Postural Orthostatic Tachycardia Syndrome (POTS) is defined as the presence of symptoms of orthostatic intolerance for at least 6 months accompanied by a heart rate increase of at least 30 beats/min within 5-30 minutes of assuming an upright posture. This normally occurs in the absence of orthostatic hypotension (a fall in blood pressure >20/10 mmHg). POTS reflects an autonomic imbalance and can be associated with severe functional disability causing limitations across multiple domains of quality of life, including physical, social, and role functioning.

In order to assess POTS, subjects are first dark-adapted and in a supine position to obtain baseline values (e.g. baseline pupil size) After ten minutes or so, a reading is taken in each eye. After which the subject stands for 10 minutes and another reading is performed. Herein, the reading is referring to capturing video images of the eye, processing the video images, and calculating values of the at least six pupillometric measures noted above. The following results were obtained based on the reading taken in each eye with regard to the assessment of POTS.

It was observed that among POTS patients, pupillometry at baseline revealed that the percent change of pupil diameter from its maximum to minimum diameter (CON) was significantly lower, as was the constriction velocity (ACV) when compared to the healthy controls. Additionally, it was found that the latency (LAT), which is the response time of the pupil after the presentation of a stimulus, was higher in POTS patients than healthy controls. The magnitude of these differences can be seen in Table 1.

TABLE 1

Comparison of Experimental and Control values for Trial 1

|     | Experimental | Control | p-value |
| --- | --- | --- | --- |
| CON | −0.31 | −0.35 | .009855 |
| ACV | −3.26 | −3.62 | .00376 |
| LAT | 0.25 | 0.23 | .027015 |

The p-value is the probability of obtaining a test statistic result at least as extreme or as close to the one that was actually observed, assuming that the null hypothesis is true.

Under orthostatic stress it was found that POTS patients experienced a decrease in maximum pupil diameter by 2.5% and minimum pupil diameter by 6.7%. Constriction percentage was found to increase by 8.5% and average constriction velocity also increased by 7.3%. These percentage values are a comparison between measurements in a supine position and an upright position. The impact of various therapeutic interventions can therefore be objectively monitored after diagnosis by determining the impact on these parameters.

Diabetic neuropathy can be detected when there is a significant reduction in the pupil to iris ratio and/or a significant increase in the latency.

Figure 4:
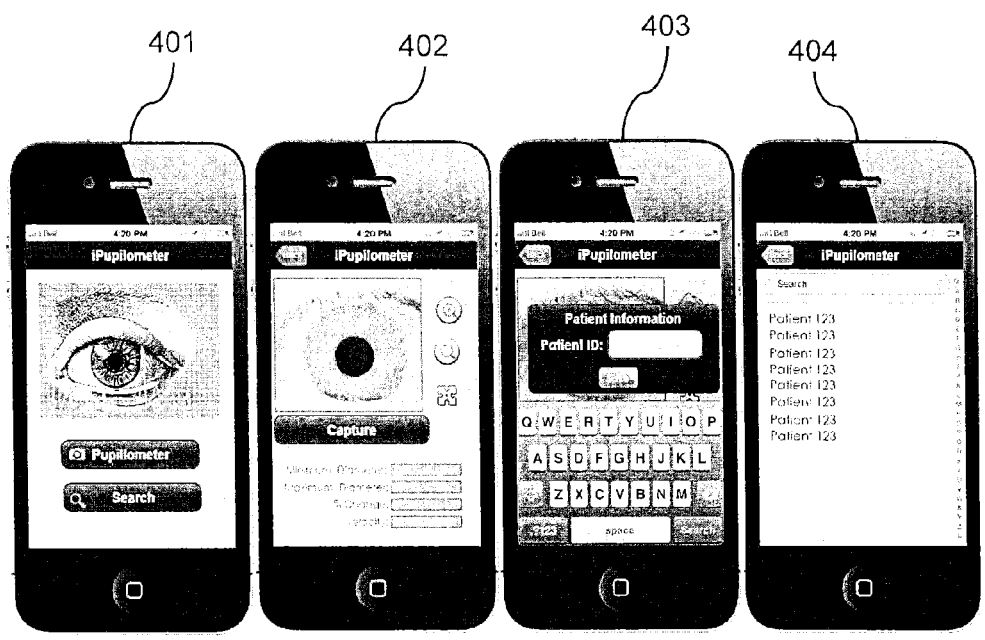
FIG. 4 illustrates an application design that acquires and processes videos and displays computer clinical parameters on a mobile device according to an exemplary embodiment.

FIG. 4 illustrates an application design that acquires and processes videos and displays computer clinical parameters on a smartphone device. For example, a smartphone device displays a first screen 401 of the application design that allows a user to use the pupillometer (mount interface 300 and the application to process the at least six pupillometric measures noted above) to capture video images of the eye, including the iris and the pupil. Further, the first screen 401 on a smartphone device 400 also allows a user to search for previously stored video images (both raw images and processed images, including parameters discussed with regard to FIGS. 2 and 3). A second screen 402 on a smartphone device illustrates a capture of an eye and also a minimum diameter and a maximum diameter. The minimum diameter and maximum diameter can be either of the pupil or the iris.

Although only a minimum diameter and a maximum diameter are illustrated on the second screen 402, it should be understood that other measurements of the iris and pupil (for example the at least six pupillometric measures noted above) can be displayed on the second screen 402. Additionally, the second screen 402 also illustrates a % change in the diameter of the pupil/iris. The % change can also correspond to a change in constriction and dilation velocities of the pupil. Finally, the second screen 402 illustrates a velocity corresponding to a current velocity of the constriction and dilation of the pupil.

The third screen 403 on the smartphone device illustrates a step for saving information regarding a patient and the fourth screen 404 illustrates a search feature to search for information on a patient. All patient information can be stored in a separate electronic database (not shown).

Figure 5:
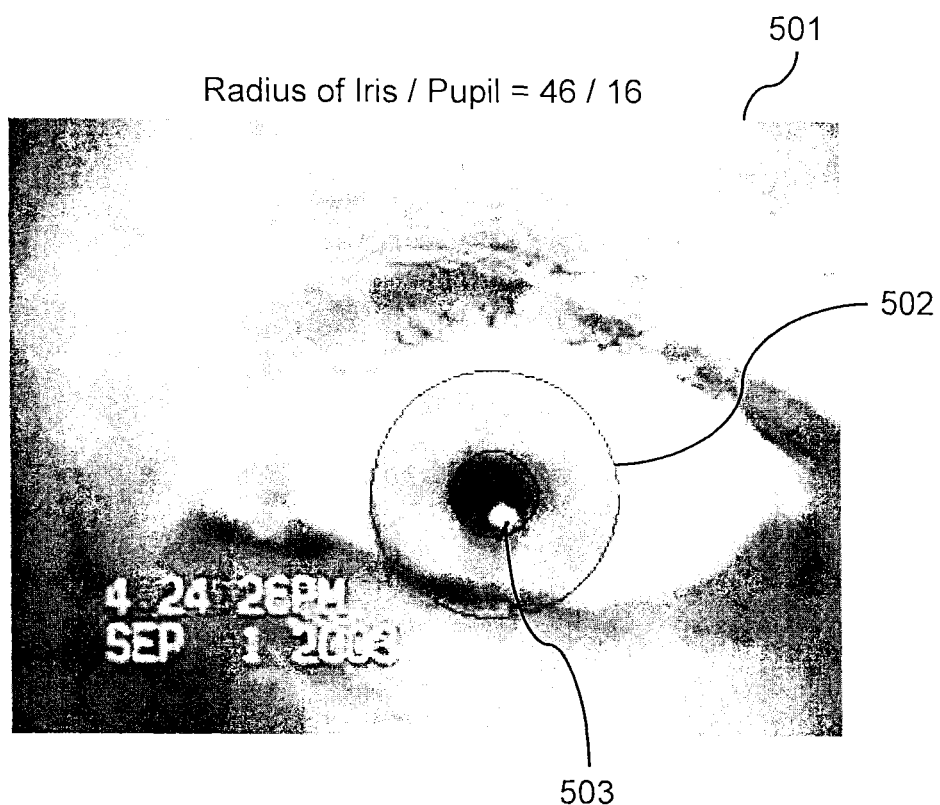
FIG. 5 illustrates a pupil and iris detection overlaid on an image frame according to an exemplary embodiment.

FIG. 5 illustrates a pupil and iris detection overlaid on an image frame 501. The circle 502 represents an estimate of the iris and circle 503 represents an estimate of the pupil. Circles 502 and 503 represent estimates of the iris and pupil, respectively, which have been calculated using the steps in FIG. 2.

The present embodiments provide features for stable performance across varying pupil colors and contrast palette. Additionally, the present embodiments are robust to handle any possible motion (blinking, translation, etc.) of the eye. Finally, the present embodiments also provide a user-friendly graphical interface to display video and extracted measurements and to improve usability in the clinic. The present embodiments provide a convenient, stable, and cost effect platform.

Another advantage of the present embodiments is that the present embodiments allow tracking of patients using opioids. According, with an application of the present embodiments, it is possible to identify patients on opioid therapy and possible abuse from opioid use. That is, the present embodiments can be used to detect if a patient is using a dose beyond the dose prescribed.

The present embodiments also allow for detection of opioid tolerance and opioid-induced hyperalgesia. The present embodiments can also be used to detect if a patients is responsive to opioid therapy. Some different genotypes of cytochrome enzymes do not allow adequate opioid metabolism, transforming pro-drugs in active metabolite. The cytochrome P450 metabolite enzymes have been implicated in the metabolism of opioid drugs, and variants in these enzymes, specifically the CYP2D6 have been linked to toxicity and therapeutic efficacy of opioids. A method of the present embodiments for opioid efficacy tracking can identify specific phenotypes based in pupillary changes and allow individualizing the treatment.

The present embodiments can also be used to detect opioid withdrawal symptoms based in pupillary changes, to detect efficacy of the treatment of abstinence syndrome, to detect neonatal abstinence syndrome when mothers were exposed to opioids or heroin during pregnancy, and to support analgesia nociception analysis assessing effectiveness of regional anesthesia in anesthetized patients.

The method of the present embodiments can also be used for management of methadone use. Methadone dose management is subjective based on clinician judgment. The method of the present embodiments allow the transition from morphine or any other opioid to methadone based on pupillary objective measurements, increasing safety and efficacy. Additionally, the method of the present embodiments can also be used to assess pupillary reactivity during cardiopulmonary resuscitation (CPR), pupillary light reflex and the magnitude of pupillary dynamic changes during CPR as objective measurements for predicting neurologic recovery after cardiac arrest.

The method of the present embodiments can be used to assess the magnitude of response to noxious stimulus tracking pupillary parameters in patients sedated or under general anesthesia, to assess very subtle changes in pupillary parameters that will be used as indicators of cognitive activity (providing an assessment for alertness and cognitive status assessment), to assess concussion severity in the sports field, and to assess changes in the intracranial pressure (ICP) after a traumatic brain injury (TBI). Pupillary parameters are sensitive indicators of ICP changes. The method of the present embodiments enable health care providers to indicate surgery or conservative clinical treatment. This tool can work as a prognostic indicator and can be used by first responders and in the war battle field as well as in emergency departments and intensive care units (ICU).

The method of the present embodiments can be used to define the association between psychotropic drugs use and overdose and pupillary changes and outcomes from drug overdose based in pupillary changes. Additionally, the method of the present embodiments can also be used to define outcomes based in pupillary changes after an ingestion of cholinergic poisons, such as carbamate and organophosphorate. This method can be designed to track pupillary changes before and during the treatment and to guide the treatment.

The method can be developed to work as triage test in drivers suspected to be under influence of alcohol or controlled substances. If there any unusual pupillary response during the test, the driver will be submitted to other tests.

Further, the method of the present embodiments can be used to help identify the drug and treatment efficacy after childhood and adults poisoning (pupillary changes can identify if the treatment was efficient and will help to define which drug was used), to compare right and left pupil will serve as a screening tool for abnormalities related to diseases and conditions of the eye such eye infections, brain trauma and tumors (anisocoria can be a red flag in many different clinical situations and this method can detect the magnitude of this condition and help to avoid serious clinical complications), and to detect pupillary changes during interview to detect lies.

Figure 6:
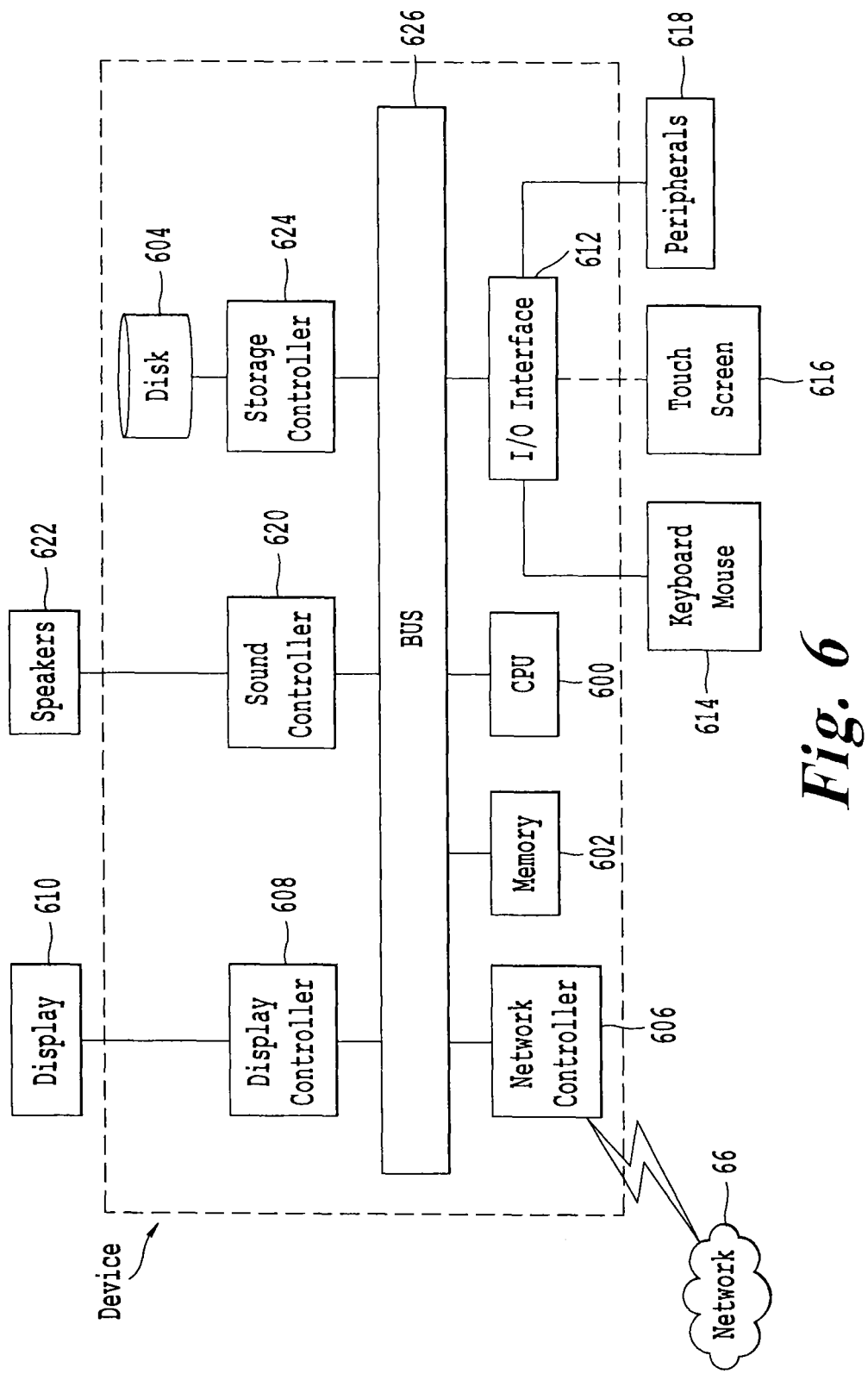
FIG. 6 illustrates an exemplary computing system.

Next, a hardware description of the device (for example, a smartphone device) according to exemplary embodiments is described with reference to FIG. 6. In FIG. 6, the device includes a CPU 600 which performs the processes described above. The process data and instructions may be stored in memory 602. These processes and instructions may also be stored on a storage medium disk 604 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the device communicates, such as a server or computer.

Further, the claimed advancements may be provided as a utility application, background daemon, or component of an operating system, or combination thereof, executing in conjunction with CPU 600 and an operating system such as Microsoft Windows 7, UNIX, Solaris, LINUX, Apple MAC-OS and other systems known to those skilled in the art.

CPU 600 may be a Xenon or Core processor from Intel of America or an Opteron processor from AMD of America, or may be other processor types that would be recognized by one of ordinary skill in the art. Alternatively, the CPU 600 may be implemented on an FPGA, ASIC, PLD or using discrete logic circuits, as one of ordinary skill in the art would recognize. Further, CPU 600 may be implemented as multiple processors cooperatively working in parallel to perform the instructions of the inventive processes described above.

The device in FIG. 6 also includes a network controller 606, such as an Intel Ethernet PRO network interface card from Intel Corporation of America, for interfacing with network 66. As can be appreciated, the network 66 can be a public network, such as the Internet, or a private network such as an LAN or WAN network, or any combination thereof and can also include PSTN or ISDN sub-networks. The network 66 can also be wired, such as an Ethernet network, or can be wireless such as a cellular network including EDGE, 3G and 4G wireless cellular systems. The wireless network can also be WiFi, Bluetooth, or any other wireless form of communication that is known.

The device further includes a display controller 608, such as a NVIDIA GeForce GTX or Quadro graphics adaptor from NVIDIA Corporation of America for interfacing with display 610, such as a Hewlett Packard HPL2445w LCD monitor. A general purpose I/O interface 612 interfaces with a keyboard and/or mouse 614 as well as a touch screen panel 616 on or separate from display 610. General purpose I/O interface also connects to a variety of peripherals 618 including printers and scanners, such as an OfficeJet or DeskJet from Hewlett Packard.

A sound controller 620 is also provided in the device, such as Sound Blaster X-Fi Titanium from Creative, to interface with speakers/microphone 622 thereby providing sounds and/or music.

The general purpose storage controller 624 connects the storage medium disk 604 with communication bus 626, which may be an ISA, EISA, VESA, PCI, or similar, for interconnecting all of the components of the device. A description of the general features and functionality of the display 610, keyboard and/or mouse 614, as well as the display controller 608, storage controller 624, network controller 606, sound controller 620, and general purpose I/O interface 612 is omitted herein for brevity as these features are known.

Obviously, numerous modifications and variations of the present disclosure are possible in light of the above teachings. It is therefore to be understood that within the scope of the appended claims, the embodiment may be practiced otherwise than as specifically described herein. For example, advantageous results may be achieved if the steps of the disclosed techniques were performed in a different sequence, if components in the disclosed systems were combined in a different manner, or if the components were replaced or supplemented by other components. The functions, processes, and algorithms described herein may be performed in hardware or software executed by hardware, including computer processors and/or programmable processing circuits configured to execute program code and/or computer instructions to execute the functions, processes, and algorithms described herein. A processing circuit includes a programmed processor, as a processor includes circuitry. A processing circuit also includes devices such as an application specific integrated circuit (ASIC) and conventional circuit components arranged to perform the recited functions.

The functions and features described herein may also be executed by various distributed components of a system. For example, one or more processors may execute these system functions, wherein the processors are distributed across multiple components communicating in a network. The distributed components may include one or more client and/or server machines, in addition to various human interface and/or communication devices (e.g., display monitors, smart phones, tablets, personal digital assistants (PDAs)). The network may be a private network, such as a LAN or WAN, or may be a public network, such as the Internet. Input to the system may be received via direct user input and/or received remotely either in real-time or as a batch process. Additionally, some implementations may be performed on modules or hardware not identical to those described. Accordingly, other implementations are within the scope that may be claimed.

It must be noted that, as used in the specification and the appended claims, the singular forms "a," "an," and "the" include plural referents unless the context clearly dictates otherwise.

While certain embodiments have been described, these embodiments have been presented by way of example only, and are not intended to limit the scope of the inventions. Indeed, the novel methods, apparatuses and systems described herein can be embodied in a variety of other forms; furthermore, various omissions, substitutions and changes in the form of the methods, apparatuses and systems described herein can be made without departing from the spirit of the inventions. The accompanying claims and their equivalents are intended to cover such forms or modifications as would fall within the scope and spirit of the inventions.

The invention claimed is:

1. A method comprising:
acquiring a video sequence, including a plurality of video frames, of an eye of a patient;
selecting and assigning weights to at least one static eye-related parameter and at least one dynamic eye-related parameter of a plurality of eye-related parameters, including a baseline pupil size, a maximum change in size of a pupil, an average velocity of constriction of the pupil, a maximum velocity of constriction of the pupil, latency of constriction of the pupil, and a velocity of re-dilation of the pupil, based on which physiologic perturbation of a patient, of a plurality of selectable physiologic perturbations, is selected to be determined; and
determining, using processing circuitry, whether the patient has the selected physiologic perturbation based on the selected at least one static eye-related parameter and the at least one dynamic eye-related parameter and the weights assigned to the at least one static eye-related parameter and the at least one dynamic eye-related parameter.

2. The method of claim 1, further comprising:
localizing, in a first frame among the plurality of video frames, a center of the pupil and two points on a boundary of the pupil and an iris of the patient;
generating, using the processing circuitry, a mask image corresponding to an expected location of the iris based on said localizing, said mask image include a plurality of pixels; and determining the at least one static eye-related parameter and the at least one dynamic eye-related parameter based on the generated mask image.

3. The method of claim 1, further comprising:
determining, using the processing circuitry, an intracranial pressure to be less than 20 mmHg when the maximum change in the size of the pupil is determined to be greater than or equal to 50%.

4. The method of claim 1, further comprising:
determining, using the processing circuitry, an intracranial pressure to be greater than 20 mmHg when the maximum change in the size of the pupil is determined to be less than or equal to 10%.

5. The method of claim 1, further comprising:
determining, using the processing circuitry, a midline shift when the maximum change in the size of the pupil is determined to be less than or equal to 10%.

6. The method of claim 1, further comprising:
determining, using the processing circuitry, an intracranial pressure to be greater than 20 mmHg when the average velocity of constriction of the pupil is less than 0.6 mm/sec.

7. The method of claim 1, further comprising:
acquiring a first video sequence of the eye of the patient while the patient is in a supine position;
determining, using the processing circuitry and based on the first video sequence, a first version of the selected at least one static eye-related parameter and the at least one dynamic eye-related parameter of the plurality of eye-related parameters;
acquiring a second video sequence of the eye of the patient while the patient is in an upright position;
determining, using the processing circuitry and based on the second video sequence, a second version of the selected at least one static eye-related parameter and the at least one dynamic eye-related parameter of the plurality of eye-related parameters; and
determining, using the processing circuitry, whether the patient has postural orthostatic tachycardia syndrome (POTS) based on a comparison of the first version and the second version of the selected at least one static eye-related parameter and the at least one dynamic eye-related parameter of the plurality of eye-related parameters.

8. The method of claim 7, wherein the second video sequence is acquired a predetermined amount of time after the patient gets to the upright position from the supine position.

9. The method of claim 7, further comprising:
determining, using the processing circuitry, that the patient has POTS when the patient's maximum pupil diameter measured in the supine position is 2.5% greater than the patient's maximum pupil diameter measured in the upright position; or
determining, using the processing circuitry, that the patient has POTS when the patient's minimum pupil diameter measured in the supine position is 6.7% greater than the patient's minimum pupil diameter measured in the upright position.

10. The method of claim 7, further comprising:
determining, using the processing circuitry, that the patient has POTS when the patient's first change in size of the pupil measured in the supine position is 8.5% less than the patient's second change in size of the pupil measured in the upright position; or
determining, using the processing circuitry, that the patient has POTS when the patient's first average velocity of constriction of the pupil measured in the supine position is 7.3% less than the patient's second average velocity of constriction of the pupil measured in the upright position.

11. The method of claim 1, wherein the physiologic perturbation includes one of drug usage or a medical condition.

12. The method of claim 1, further comprising:
generating, using the processing circuitry, a mask image from a first frame among the plurality of video frames, the mask image including a plurality of pixels corresponding to the pupil of the eye of the patient;
replacing, using the processing circuitry, bright pixels from among the plurality of pixels with dark pixels to generate an updated mask image; and
determining, using the processing circuitry and based on the updated mask image, the selected at least one static eye-related parameter and the at least one dynamic eye-related parameter of the plurality of eye-related parameters.

13. The method of claim 1, further comprising:
selecting and assigning weights to all eye-related parameters of the plurality of eye-related parameters including the baseline pupil size, the maximum change in size of the pupil, the average velocity of constriction of the pupil, the maximum velocity of constriction of the pupil, latency of constriction of the pupil, and the velocity of re-dilation of the pupil based on another physiologic perturbation of the patient to be determined; and
determining whether the patient has the another physiologic perturbation based on the selected all eye-related parameters and the weights assigned to the all eye-related parameters.

14. An apparatus comprising:
circuitry configured to:
acquire a video sequence, including a plurality of video frames, of an eye of a patient;
select and assign weights to at least one static eye-related parameter and at least one dynamic eye-related parameter of a plurality of eye-related parameters, including a baseline pupil size, a maximum change in size of a pupil, an average velocity of constriction of the pupil, a maximum velocity of constriction of the pupil, latency of constriction of the pupil, and a velocity of re-dilation of the pupil, based on which physiologic perturbation of a patient, of a plurality of selectable physiologic perturbations, is selected to be determined; and
determine whether the patient has the selected physiologic perturbation based on the selected at least one static eye-related parameter and the at least one dynamic eye-related parameter and the weights assigned to the at least one static eye-related parameter and the at least one dynamic eye-related parameter.

15. The apparatus of claim 14, wherein the circuitry is further configured to:
determine an intracranial pressure to be less than 20 mmHg when the maximum change in the size of the pupil is determined to be greater than or equal to 50%.

16. The apparatus of claim 14, wherein the circuitry is further configured to:
determine an intracranial pressure to be greater than 20 mmHg when the maximum change in the size of the pupil is determined to be less than or equal to 10%.

17. The apparatus of claim 14, wherein the circuitry is further configured to:
determine a midline shift when the maximum change in the size of the pupil is determined to be less than or equal to 10%.

18. The apparatus of claim 14, wherein the circuitry is further configured to:
determine an intracranial pressure to be greater than 20 mmHg when the average velocity of constriction of the pupil is less than 0.6 mm/sec.

19. The apparatus of claim 14, wherein the circuitry is further configured to:
acquire a first video sequence of the eye of the patient while the patient is in a supine position;
determine, based on the first video sequence, a first version of the selected at least one static eye-related parameter and the at least one dynamic eye-related parameter of the plurality of eye-related parameters;
acquire a second video sequence of the eye of the patient while the patient is in an upright position;
determine, based on the second video sequence, a second version of the selected at least one static eye-related parameter and the at least one dynamic eye-related parameter of the plurality of eye-related parameters; and
determine whether the patient has postural orthostatic tachycardia syndrome (POTS) based on a comparison of the first version and the second version of the selected at least one static eye-related parameter and the at least one dynamic eye-related parameter of the plurality of eye-related parameters.

20. The apparatus of claim 19, wherein the second video sequence is acquired a predetermined amount of time after the patient gets to the upright position from the supine position.

21. The apparatus of claim 19, wherein the circuitry is further configured to:
determine that the patient has POTS when the patient's maximum pupil diameter measured in the supine position is 2.5% greater than the patient's maximum pupil diameter measured in the upright position; or
determine that the patient has POTS when the patient's minimum pupil diameter measured in the supine position is 6.7% greater than the patient's minimum pupil diameter measured in the upright position.

22. The apparatus of claim 19, wherein the circuitry is further configured to:
determine that the patient has POTS when the patient's first change in size of the pupil measured in the supine position is 8.5% less than the patient's second change in size of the pupil measured in the upright position; or
determine that the patient has POTS when the patient's first average velocity of constriction of the pupil measured in the supine position is 7.3% less than the patient's second average velocity of constriction of the pupil measured in the upright position.

23. The apparatus of claim 14, wherein the physiologic perturbation includes one of drug usage or a medical condition.

* * * * *